(12) United States Patent
Kumada et al.

(10) Patent No.: US 10,520,486 B2
(45) Date of Patent: Dec. 31, 2019

(54) METHOD FOR SUPPRESSING PROTEIN ADSORPTION

(71) Applicants: NATIONAL UNIVERSITY CORPORATION KYOTO INSTITUTE OF TECHNOLOGY, Kyoto-shi, Kyoto (JP); NOF CORPORATION, Shibuya-ku, Tokyo (JP)

(72) Inventors: Yoichi Kumada, Kyoto (JP); Yasutaka Kawaguchi, Kyoto (JP); Aranna Nemoto, Kyoto (JP); Fumio Nakashima, Kawasaki (JP); Nobuyuki Sakamoto, Kawasaki (JP)

(73) Assignees: National University Corporation Kyoto Institute of Technology, Kyoto-shi, Kyoto (JP); NOF Corporation, Shibuya-ku, Tokyo (JP)

( * ) Notice: Subject to any disclaimer, the term of this patent is extended or adjusted under 35 U.S.C. 154(b) by 113 days.

(21) Appl. No.: 15/550,445

(22) PCT Filed: Feb. 18, 2016

(86) PCT No.: PCT/JP2016/054677
§ 371 (c)(1),
(2) Date: Aug. 11, 2017

(87) PCT Pub. No.: WO2016/133152
PCT Pub. Date: Aug. 25, 2016

(65) Prior Publication Data
US 2018/0031537 A1 Feb. 1, 2018

(30) Foreign Application Priority Data
Feb. 19, 2015 (JP) .................................. 2015-031155

(51) Int. Cl.
| | | |
|---|---|---|
| G01N 33/00 | (2006.01) | |
| G01N 33/48 | (2006.01) | |
| C07F 9/44 | (2006.01) | |
| C08F 220/56 | (2006.01) | |
| C08F 222/38 | (2006.01) | |

(52) U.S. Cl.
CPC ........... *G01N 33/48* (2013.01); *C07F 9/4461* (2013.01); *C08F 220/56* (2013.01); *C08F 222/385* (2013.01)

(58) Field of Classification Search
CPC .................................................. G01N 33/48
USPC .................................................... 436/86
See application file for complete search history.

(56) References Cited

U.S. PATENT DOCUMENTS

| | | |
|---|---|---|
| 2008/0312394 A1 | 12/2008 | Tamori et al. |
| 2009/0130776 A1 | 5/2009 | Imamura et al. |
| 2010/0016506 A1 | 1/2010 | Tamori et al. |
| 2010/0204424 A1 | 8/2010 | Tamori et al. |

FOREIGN PATENT DOCUMENTS

| | | | | |
|---|---|---|---|---|
| JP | 04-009665 A | 1/1992 | | |
| JP | 05-312807 A | 11/1993 | | |
| JP | H07-083923 | 3/1995 | | |
| JP | 2002-356519 A | 12/2002 | | |
| JP | 2003-344406 A | 12/2003 | | |
| JP | 2005300313 A | * | 10/2005 | ........... G01N 33/531 |
| JP | 2006-258585 A | 9/2006 | | |
| JP | 2007-091736 A | 4/2007 | | |
| JP | 2009-019031 A | 1/2009 | | |
| JP | 2014-144394 A | 8/2014 | | |
| WO | 2008146631 A1 | 12/2008 | | |

OTHER PUBLICATIONS

Translation of JP2005300313 obtained from Espacenet on Oct. 30, 2019 (Year: 2019).*
PCT International Search Report dated Aug. 2, 2016 in connection with PCT International Application No. PCT/JP2016/054677, 5 pages.
PCT Written Opinion dated Aug. 2, 2016 in connection with PCT International Application No. PCT/JP2016/054677, 6 pages.
Sakaki S et al., entitled "Water-Soluble 2-Methacryloyloxyethyl Phosphorylcholine Copolymer as a Novel Synthetic Blocking Reagent in Immunoassay System," Polymer Journal, vol. 32, No. 8, pp. 637-641, 2000.
Hawkes, R et al., entitled "A Dot-Immunobinding Assay for Monoclonal and Other Antibodies," Analytical Biochemistry, 119, 142-147, 1982.

* cited by examiner

*Primary Examiner* — Christopher Adam Hixson
*Assistant Examiner* — Emily R. Berkeley
(74) *Attorney, Agent, or Firm* — Amster, Rothstein & Ebenstein LLP

(57) ABSTRACT

Provided is a novel method of suppressing non-specific protein adsorption. The above-mentioned object can be achieved by treating a solid phase with a solid phase-treating liquid containing a phosphorylcholine group-containing polymer as a main component, and treating a specimen with a specimen-treating liquid containing, as a main component, a polymer having a phosphorylcholine group, a hydroxy group, and a hydrophobic group, followed by addition of the treated specimen to the treated solid phase.

7 Claims, No Drawings

METHOD FOR SUPPRESSING PROTEIN ADSORPTION

CROSS-REFERENCE TO RELATED APPLICATIONS

This application is a U.S. national stage entry under 35 U.S.C. § 371 of PCT International Patent Application No. PCT/JP2016/054677, filed Feb. 18, 2016, which claims priority to Japanese Patent Application No. 2015-031155, filed Feb. 19, 2015, the contents of which are incorporated by reference herein into the subject application.

TECHNICAL FIELD

The present invention relates to a method of suppressing non-specific protein adsorption, and more specifically, to a method of suppressing protein adsorption involving using a solid phase-treating liquid containing a phosphorylcholine group-containing polymer as a main component, and a specimen-treating liquid containing, as a main component, a polymer having a phosphorylcholine group, a hydroxy group, and a hydrophobic group.

The present application claims priority from Japanese Patent Application No. 2015-031155, which is incorporated herein by reference.

BACKGROUND ART

In the fields of clinical laboratory tests and diagnostic drugs, measurement methods involving utilizing immune reactions are widely performed. In this context, there is a demand for an increase in sensitivity of a test, and an improvement in sensitivity of a clinical laboratory test or a diagnostic drug has become a significant task. In order to increase the sensitivity, as a mode of detection, a method involving using an enzymatic reaction with peroxidase or alkaline phosphatase is being replaced by a method involving using fluorescence or chemiluminescence. It is said that the use of fluorescence or chemiluminescence as the mode of detection allows confirmation of the presence of one molecule of a test object substance in theory. In actuality, however, target sensitivity has not been achieved.

As one of the factors affecting the detection sensitivity in measurement utilizing an immune reaction, there is given non-specific adsorption of an antibody or an antigen serving as a measurement object, or a labeled form thereof to be utilized for the measurement onto an immune reaction vessel or a solid phase surface. In addition, when a substance in which a plurality of kinds of biomolecules coexist, such as serum, plasma, cell extract, and urine, is used as a specimen, occurrence of a noise due to non-specific adsorption of an unspecified large number of coexisting substances, such as various proteins, onto the immune reaction vessel or the solid phase surface also serves as a factor in inhibiting the increase in sensitivity.

In order to prevent such non-specific adsorption, heretofore, there has been used a method of suppressing non-specific protein adsorption by allowing a protein of biological origin, such as bovine serum albumin, casein, or gelatin, that is not involved in the immune reaction to adsorb onto the immune reaction vessel or the solid phase surface. However, when the protein of biological origin, such as bovine serum albumin, is used, there are restrictions, such as a problem of biological contamination typified by BSE, a lot-to-lot variation, a storage temperature, and an expiration date. Accordingly, there has been desired development of a non-specific protein adsorption-suppressing agent containing, as a main component, a chemically synthesized product capable of solving those problems.

As the non-specific protein adsorption-suppressing agent containing a chemically synthesized product as a main component, the following has been disclosed.

In Patent Literature 1, there is a disclosure of a "blocking agent containing polyvinyl alcohol." In Patent Literature 2, there is a disclosure of a "protein adsorption-preventing agent containing a 2-methacryloyloxyethylphosphorylcholine polymer."

Those methods each express an effect solely by allowing the chemically synthesized product serving as the non-specific protein adsorption-suppressing agent to physically adsorb onto the solid phase surface. Those techniques can preclude non-specific adsorption onto the solid phase surface to some extent, but have not yet been sufficient. Further, a specimen-treating liquid of the present invention is not disclosed or suggested.

CITATION LIST

Patent Literature

[PTL 1] JP 04-19561 A
[PTL 2] JP 07-83923 A

SUMMARY OF INVENTION

Technical Problem

As apparent from the foregoing, an object of the present invention is to provide a novel method of suppressing non-specific protein adsorption.

Solution to Problem

The inventors of the present invention have made extensive investigations in order to achieve the above-mentioned object, and as a result, have found that the object can be achieved by treating a solid phase with a solid phase-treating liquid containing a phosphorylcholine group-containing polymer as a main component, and treating a specimen with a specimen-treating liquid containing, as a main component, a polymer having a phosphorylcholine group, a hydroxy group, and a hydrophobic group, followed by addition of the treated specimen to the treated solid phase. Thus, the inventors have completed the present invention.

That is, the present invention is as described below.

1. A method of suppressing non-specific protein adsorption, the method including the steps of:

(i) treating a solid phase with a solid phase-treating liquid containing a phosphorylcholine group-containing polymer as a main component; and (ii) treating a specimen with a specimen-treating liquid containing, as a main component, a polymer having a phosphorylcholine group, a hydroxy group, and a hydrophobic group, followed by addition of the treated specimen to the solid phase treated in the step (i), or (iii) treating a specimen with a specimen-treating liquid containing, as a main component, a polymer having a phosphorylcholine group, a hydroxy group, and a hydrophobic group; and (iv) treating a solid phase with a solid phase-treating liquid containing a phosphorylcholine group-containing polymer as a main component, followed by addition of the specimen treated in the step (iii) to the treated solid phase.

2. A method of suppressing non-specific protein adsorption according to the above-mentioned item 1, in which a combination of the phosphorylcholine group-containing polymer, and the polymer having a phosphorylcholine group, a hydroxy group, and a hydrophobic group includes any one or more of the following:

(1) a combination of
a phosphorylcholine group-containing polymer which contains, as constituent units, 2-methacryloyloxyethylphosphorylcholine, butyl methacrylate, and glycerol methacrylate, and
a polymer having a phosphorylcholine group, a hydroxy group, and a hydrophobic group, which contains, as constituent units, 2-methacryloyloxyethylphosphorylcholine, butyl methacrylate, and glycerol methacrylate;

(2) a combination of
a phosphorylcholine group-containing polymer which contains, as constituent units, 2-methacryloyloxyethylphosphorylcholine, butyl methacrylate, and hydroxyethyl methacrylate, and
a polymer having a phosphorylcholine group, a hydroxy group, and a hydrophobic group, which contains, as constituent units, 2-methacryloyloxyethylphosphorylcholine, butyl methacrylate, and glycerol methacrylate;

(3) a combination of
a phosphorylcholine group-containing polymer which contains, as constituent units, 2-methacryloyloxyethylphosphorylcholine and butyl methacrylate, and
a polymer having a phosphorylcholine group, a hydroxy group, and a hydrophobic group, which contains, as constituent units, 2-methacryloyloxyethylphosphorylcholine, butyl methacrylate, and glycerol methacrylate;

(4) a combination of
a phosphorylcholine group-containing polymer which contains, as constituent units, 2-methacryloyloxyethylphosphorylcholine and butyl methacrylate, and
a polymer having a phosphorylcholine group, a hydroxy group, and a hydrophobic group, which contains, as constituent units, 2-methacryloyloxyethylphosphorylcholine, butyl methacrylate, and hydroxyethyl methacrylate;

(5) a combination of
a phosphorylcholine group-containing polymer which contains, as constituent units, 2-methacryloyloxyethylphosphorylcholine and glycerol methacrylate, and
a polymer having a phosphorylcholine group, a hydroxy group, and a hydrophobic group, which contains, as constituent units, 2-methacryloyloxyethylphosphorylcholine, butyl methacrylate, and glycerol methacrylate; and (6) a combination of
a phosphorylcholine group-containing polymer which contains, as constituent units, 2-methacryloyloxyethylphosphorylcholine and hydroxyethyl methacrylate, and
a polymer having a phosphorylcholine group, a hydroxy group, and a hydrophobic group, which contains, as constituent units, 2-methacryloyloxyethylphosphorylcholine, butyl methacrylate, and hydroxyethyl methacrylate.

Advantageous Effects of Invention

In the method of suppressing non-specific protein adsorption of the present invention, the polymers contained in the solid phase-treating liquid and specimen-treating liquid used, which are chemically synthesized products, have high non-specific protein adsorption-suppressing abilities. Therefore, the method can be used as a substitute for the non-specific protein adsorption-suppressing agent of biological origin remaining in use despite problems such as a lot-to-lot variation and biological contamination.

DESCRIPTION OF EMBODIMENTS

A method of suppressing non-specific protein adsorption of the present invention (hereinafter sometimes referred to as "method of the present invention") includes the steps of:

(i) treating a solid phase with a solid phase-treating liquid containing a phosphorylcholine group-containing polymer as a main component; and (ii) treating a specimen with a specimen-treating liquid containing, as a main component, a polymer having a phosphorylcholine group, a hydroxy group, and a hydrophobic group, followed by addition of the treated specimen to the solid phase treated in the step (i), or (iii) treating a specimen with a specimen-treating liquid containing, as a main component, a polymer having a phosphorylcholine group, a hydroxy group, and a hydrophobic group; and (iv) treating a solid phase with a solid phase-treating liquid containing a phosphorylcholine group-containing polymer as a main component, followed by addition of the specimen treated in the step (iii) to the treated solid phase.

Now, the method of the present invention is described in more detail.

The method of the present invention may be used in, for example, an immunoassay involving measurement utilizing an enzymatic reaction or an antigen-antibody reaction of an immunoglobulin utilizing a protein, a polypeptide, a steroid, a lipid, a hormone, or the like, more specifically any of various antigens, antibodies, receptors, enzymes, and the like.

Specifically, the method may be applied to known radioimmunoassay (RIA), enzyme immunoassay (EIA), fluoroimmunoassay (FIA), chemiluminescence immunoassay (CLIA), latex turbidimetry, or the like, particularly preferably to enzyme immunoassay (EIA), fluoroimmunoassay (FIA), chemiluminescence immunoassay (CLIA), latex turbidimetry, western blotting, or the like.

In each of those known immunoassays, an antibody or an antigen is allowed to bind onto a solid phase surface, and then a solid phase surface without the antibody or the antigen binding thereonto is treated with the solid phase-treating liquid. Meanwhile, a specimen is treated with the specimen-treating liquid. Thus, non-specific protein adsorption is suppressed.

The "solid phase" of the present invention means a site where an immune reaction is to be performed (reaction vessel). In particular, onto the solid phase surface, an enzyme, an antibody, an antigen, a peptide, or the like to be involved in the immune reaction can be immobilized through physical adsorption, chemical binding, biological binding, or the like.

A material for the solid phase is not particularly limited, and examples thereof may include polystyrene, polyvinyl chloride, polypropylene, polycarbonate, polymethyl methacrylate, glass, a metal, ceramic, a silicon rubber, a polyvinylidene fluoride film (hereinafter referred to as "PVDF film"), a nylon film, and a nitrocellulose film. Of those, polystyrene, polymethyl methacrylate, and polycarbonate are preferred, and polystyrene is particularly preferred. In addition, the forms of those materials are not particularly limited, and examples thereof may include a test tube, a titer plate, a latex, and magnetic fine particles.

The "specimen" of the present invention means a sample in which a plurality of kinds of biomolecules coexist, such as whole blood, serum, plasma, cell extract, lacrimal fluid, saliva, urine, or feces, but is not particularly limited.

The "solid phase-treating liquid" of the present invention is a solution for treating a solid phase, particularly, for bringing the solid phase-treating liquid into contact with a solid phase surface. The solution contains as a main component at least a phosphorylcholine group-containing polymer. The solid phase-treating liquid of the present invention is not particularly limited as long as the solid phase-treating liquid contains a phosphorylcholine group-containing polymer. The solid phase-treating liquid contains, for example, one or more of the following polymers.

2-Methacryloyloxyethylphosphorylcholine (MPC: phosphorylcholine group-containing polymer)

Copolymer of MPC, butyl methacrylate (BMA: polymer having a hydrophobic group), and glycerol methacrylate (Gr: polymer having a hydroxy group) (MPC-BMA-Gr)

Copolymer of MPC, BMA, and hydroxyethyl methacrylate (HMA: polymer having a hydroxy group) (MPC-BMA-HMA)

Copolymer of MPC and Gr (MPC-Gr)
Copolymer of MPC and HMA (MPC-HMA)
Copolymer of MPC and BMA (MPC-BMA)
Copolymer of MPC and stearyl methacrylate (SMA: polymer having a hydrophobic group) (MPC-SMA)
Copolymer of MPC and lauryl methacrylate (LMA: polymer having a hydrophobic group) (MPC-LMA)

The compositional ratio (molar ratio) of MPC in each of the above-mentioned phosphorylcholine group-containing polymers is not particularly limited, but is from 1% to 100%, preferably from 5% to 100%, more preferably from 20% to 80%.

As a solvent of the solid phase-treating liquid of the present invention, any buffers that may be used for immunoassays and pure water may all be used. For example, a phosphate buffer, an acetate buffer, a carbonate buffer, a citrate buffer, a Tris buffer, a HEPES buffer, or physiological saline may be used. However, the solvent is not particularly limited.

In addition, the concentration of the solid phase-treating liquid of the present invention is preferably from 0.0125 wt % to 5.0 wt % (in terms of weight of all polymers), more preferably from 0.1 wt % to 0.5 wt %.

The "specimen-treating liquid" of the present invention is a solution for treating a specimen, the solution containing, as a main component, at least a polymer having a phosphorylcholine group, a hydroxy group, and a hydrophobic group. The treating a specimen means, for example, diluting the specimen with the specimen-treating liquid, adding the specimen to the specimen-treating liquid, or adding the specimen-treating liquid to the specimen.

The specimen-treating liquid of the present invention is not particularly limited as long as the specimen-treating liquid contains a polymer having a phosphorylcholine group, a hydroxy group, and a hydrophobic group. The specimen-treating liquid contains, for example, one or more of the following polymers.

Copolymer of MPC, BMA, and Gr (MPC-BMA-Gr)
Copolymer of MPC, BMA, and HMA (MPC-BMA-HMA)
Copolymer of MPC, BMA, and hydroxypropyl methacrylate (HPM: polymer having a hydroxy group) (MPC-BMA-HPM)
Copolymer of MPC, SMA, and Gr (MPC-SMA-Gr)
Copolymer of MPC, SMA, and HMA (MPC-SMA-HMA)
Copolymer of MPC, SMA, and HPM (MPC-SMA-HPM)
Copolymer of MPC, LMA, and Gr (MPC-LMA-Gr)
Copolymer of MPC, LMA, and HMA (MPC-LMA-HMA)
Copolymer of MPC, LMA, and HPM (MPC-LMA-HPM)

The compositional ratio (molar ratio) of MPC in each of the above-mentioned polymers having a phosphorylcholine group, a hydroxy group, and a hydrophobic group is not particularly limited, but is from 1% to 95%, preferably from 5% to 80%, more preferably from 10% to 60%.

As a solvent of the specimen-treating liquid of the present invention, any buffers that may be used for immunoassays and pure water may all be used. For example, a phosphate buffer, an acetate buffer, a carbonate buffer, a citrate buffer, a Tris buffer, a HEPES buffer, or physiological saline may be used. However, the solvent is not particularly limited.

In addition, the concentration of the specimen-treating liquid of the present invention is preferably from 0.0125 wt % to 5.0 wt % (in terms of weight of all polymers), more preferably from 0.1 wt % to 0.5 wt %.

In the method of the present invention, first, the solid phase-treating liquid containing a phosphorylcholine group-containing polymer as a main component is added to a solid phase surface {resin vessel for an immunoassay (e.g., titer plate)}. In more detail, the solid phase-treating liquid is added, after an antibody or an antigen has been allowed to bind onto the solid phase surface, to the solid phase. Meanwhile, the specimen is diluted with the specimen-treating liquid containing, as a main component, a polymer having a phosphorylcholine group, a hydroxy group, and a hydrophobic group, and the specimen is added to the treated solid phase surface. In more detail, the specimen-treating liquid may be added to a reagent to be added in measurement, or may be added to the specimen. Specifically, the specimen-treating liquid is added to and mixed with serum containing a substance to be detected, or a reagent containing a labeled antibody or a labeled antigen, or all of the foregoing. Further, even when adsorption of the substance to be detected in the serum serving as the specimen onto the solid phase is not a problem, the specimen-treating liquid may be mixed at the time of the addition of a labeled antibody or a labeled antigen. Through those operations, non-specific adsorption of a protein other than the target (protein other than the substance to be detected) contained in the specimen can be suppressed.

A combination of the phosphorylcholine group-containing polymer serving as the main component of the solid phase-treating liquid, and the polymer having a phosphorylcholine group, a hydroxy group, and a hydrophobic group serving as the main component of the specimen-treating liquid may be specifically exemplified by the following, but is not particularly limited (a polymer on the left represents the phosphorylcholine group-containing polymer, and a polymer on the right represents the polymer having a phosphorylcholine group, a hydroxy group, and a hydrophobic group).

MPC and MPC-BMA-Gr
MPC and MPC-BMA-HMA
MPC and MPC-BMA-HPM
MPC and MPC-SMA-Gr
MPC and MPC-SMA-HMA
MPC and MPC-SMA-HPM
MPC and MPC-LMA-Gr
MPC and MPC-LMA-HMA
MPC and MPC-LMA-HPM
MPC-BMA-Gr and MPC-BMA-Gr
MPC-BMA-Gr and MPC-BMA-HMA
MPC-BMA-Gr and MPC-BMA-HPM MPC-BMA-Gr and MPC-SMA-Gr
MPC-BMA-Gr and MPC-SMA-HMA
MPC-BMA-Gr and MPC-SMA-HPM
MPC-BMA-Gr and MPC-LMA-Gr
MPC-BMA-Gr and MPC-LMA-HMA
MPC-BMA-Gr and MPC-LMA-HPM
MPC-BMA-HMA and MPC-BMA-Gr
MPC-BMA-HMA and MPC-BMA-HMA
MPC-BMA-HMA and MPC-BMA-HPM
MPC-BMA-HMA and MPC-SMA-Gr
MPC-BMA-HMA and MPC-SMA-HMA
MPC-BMA-HMA and MPC-SMA-HPM
MPC-BMA-HMA and MPC-LMA-Gr
MPC-BMA-HMA and MPC-LMA-HMA
MPC-BMA-HMA and MPC-LMA-HPM
MPC-Gr and MPC-BMA-Gr
MPC-Gr and MPC-BMA-HMA
MPC-Gr and MPC-BMA-HPM
MPC-Gr and MPC-SMA-Gr
MPC-Gr and MPC-SMA-HMA
MPC-Gr and MPC-SMA-HPM
MPC-Gr and MPC-LMA-Gr
MPC-Gr and MPC-LMA-HMA
MPC-Gr and MPC-LMA-HPM
MPC-HMA and MPC-BMA-Gr
MPC-HMA and MPC-BMA-HMA
MPC-HMA and MPC-BMA-HPM
MPC-HMA and MPC-SMA-Gr
MPC-HMA and MPC-SMA-HMA
MPC-HMA and MPC-SMA-HPM
MPC-HMA and MPC-LMA-Gr
MPC-HMA and MPC-LMA-HMA
MPC-HMA and MPC-LMA-HPM
MPC-BMA and MPC-BMA-Gr
MPC-BMA and MPC-BMA-HMA
MPC-BMA and MPC-BMA-HPM
MPC-BMA and MPC-SMA-Gr
MPC-BMA and MPC-SMA-HMA
MPC-BMA and MPC-SMA-HPM
MPC-BMA and MPC-LMA-Gr
MPC-BMA and MPC-LMA-HMA
MPC-BMA and MPC-LMA-HPM
MPC-SMA and MPC-BMA-Gr
MPC-SMA and MPC-BMA-HMA
MPC-SMA and MPC-BMA-HPM
MPC-SMA and MPC-SMA-Gr
MPC-SMA and MPC-SMA-HMA
MPC-SMA and MPC-SMA-HPM
MPC-SMA and MPC-LMA-Gr
MPC-SMA and MPC-LMA-HMA
MPC-SMA and MPC-LMA-HPM
MPC-LMA and MPC-BMA-Gr
MPC-LMA and MPC-BMA-HMA
MPC-LMA and MPC-BMA-HPM
MPC-LMA and MPC-SMA-Gr
MPC-LMA and MPC-SMA-HMA
MPC-LMA and MPC-SMA-HPM
MPC-LMA and MPC-LMA-Gr
MPC-LMA and MPC-LMA-HMA
MPC-LMA and MPC-LMA-HPM The compositional ratio (molar ratio) of MPC in each of the above-mentioned phosphorylcholine group-containing polymers serving as the main component of the solid phase-treating liquid is not particularly limited, but is from 1% to 100%, preferably from 5% to 100%, more preferably from 20% to 80%. The compositional ratio of the copolymerization components other than MPC is not particularly limited, but is from 99% to 0%, preferably from 95% to 0%, more preferably from 80% to 20%.

The compositional ratio (molar ratio) of MPC in each of the above-mentioned polymers having a phosphorylcholine group, a hydroxy group, and a hydrophobic group serving as the main component of the specimen-treating liquid is not particularly limited, but is from 1% to 95%, preferably from 5% to 80%, more preferably from 10% to 60%. The compositional ratio of the copolymerization components other than MPC is not particularly limited, but is from 99% to 5%, preferably from 95% to 20%, more preferably from 90% to 40%.

A more preferred combination of the phosphorylcholine group-containing polymer serving as the main component of the solid phase-treating liquid, and the polymer having a phosphorylcholine group, a hydroxy group, and a hydrophobic group serving as the main component of the specimen-treating liquid may be specifically exemplified by the following, but is not particularly limited.

A combination of a phosphorylcholine group-containing polymer which contains, as constituent units, 2-methacryloyloxyethylphosphorylcholine, butyl methacrylate, and glycerol methacrylate, and a polymer having a phosphorylcholine group, a hydroxy group, and a hydrophobic group, which contains, as constituent units, 2-methacryloyloxyethylphosphorylcholine, butyl methacrylate, and glycerol methacrylate A combination of a phosphorylcholine group-containing polymer which contains, as constituent units, 2-methacryloyloxyethylphosphorylcholine, butyl methacrylate, and hydroxyethyl methacrylate, and a polymer having a phosphorylcholine group, a hydroxy group, and a hydrophobic group, which contains, as constituent units, 2-methacryloyloxyethylphosphorylcholine, butyl methacrylate, and glycerol methacrylate A combination of a phosphorylcholine group-containing polymer which contains, as constituent units, 2-methacryloyloxyethylphosphorylcholine and butyl methacrylate, and a polymer having a phosphorylcholine group, a hydroxy group, and a hydrophobic group, which contains, as constituent units, 2-methacryloyloxyethylphosphorylcholine, butyl methacrylate, and glycerol methacrylate A combination of a phosphorylcholine group-containing polymer which contains, as constituent units, 2-methacryloyloxyethylphosphorylcholine and butyl methacrylate, and a polymer having a phosphorylcholine group, a hydroxy group, and a hydrophobic group, which contains, as constituent units, 2-methacryloyloxyethylphosphorylcholine, butyl methacrylate, and hydroxyethyl methacrylate A combination of a phosphorylcholine group-containing polymer which contains, as constituent units, 2-methacryloyloxyethylphosphorylcholine and glycerol methacrylate, and a polymer having a phosphorylcholine group, a hydroxy group, and a hydrophobic group, which contains, as constituent units, 2-methacryloyloxyethylphosphorylcholine, butyl methacrylate, and glycerol methacrylate A combination of a phosphorylcholine group-containing polymer which contains, as constituent units, 2-methacryloyloxyethylphosphorylcholine and hydroxyethyl methacrylate, and a polymer having a phosphorylcholine group, a hydroxy group, and a hydrophobic group, which contains, as constituent units, 2-methacryloyloxyethylphosphorylcholine, butyl methacrylate, and hydroxyethyl methacrylate In each of the above-mentioned more preferred combinations of the phosphorylcholine group-containing polymer serving as the main component of the solid phase-treating liquid, and the polymer having a phosphorylcholine group, a hydroxy group, and a hydrophobic group serving as the main component of the specimen-treating liquid, the compositional ratio (molar ratio) of MPC in the phosphorylcholine group-containing polymer serving as the main component of the solid phase-treating liquid is not particularly limited, but is from 1% to 99%, preferably from 5% to 99%, more preferably from 20% to 80%. The compositional ratio of the copolymerization components other than MPC is not particularly limited, but is from 99% to 1%, preferably from 95% to 1%, more preferably from 80% to 20%.

In addition, in each of the above-mentioned more preferred combinations of the phosphorylcholine group-containing polymer serving as the main component of the solid phase-treating liquid, and the polymer having a phosphorylcholine group, a hydroxy group, and a hydrophobic group serving as the main component of the specimen-treating liquid, the compositional ratio (molar ratio) of MPC in the polymer having a phosphorylcholine group, a hydroxy group, and a hydrophobic group serving as the main component of the specimen-treating liquid is not particularly limited, but is from 1% to 95%, preferably from 5% to 80%, more preferably from 10% to 60%. The compositional ratio of the copolymerization components other than MPC is not particularly limited, but is from 99% to 5%, preferably from 95% to 20%, more preferably from 90% to 40%.

In the method of the present invention, more specifically, for example, a solid phase surface to be used in any of various immunoassays may be treated with the solid phase-treating liquid after a protein, such as an enzyme or an antibody, or an antigen has been allowed to bind onto the solid phase surface. When, for example, a plate made of polystyrene is used as the solid phase surface to be treated with the solid phase-treating liquid, a solid phase surface having a non-specific protein adsorption-suppressing effect can be obtained by allowing a protein to physically adsorb or chemically bind onto the plate, washing the resultant, and then adding the solid phase-treating liquid to the solid phase.

Further, when measurement is performed using the solid phase surface having a non-specific protein adsorption-suppressing effect, the treatment with the specimen-treating liquid may be performed by mixing the specimen-treating liquid with serum containing the target substance (substance to be detected), a labeled antibody or a labeled antigen, or all of the foregoing. A method for the mixing is not particularly limited, but specifically, the specimen-treating liquid may be added to and stirred with serum containing the target substance, or a solution containing a labeled antibody or a labeled antigen. The specimen-treating liquid may be diluted with a solvent known per se before being added.

EXAMPLES

The present invention is described in more detail by way of Examples and Comparative Examples below. However, the present invention is by no means limited to the scope of Examples below.

(Synthesis of Copolymer)

Polymer compounds to be used in Examples of the present invention and polymer compounds to be used in Comparative Examples were synthesized. Specifically, a copolymer of 2-methacryloyloxyethylphosphorylcholine (MPC) and glycerol methacrylate (Gr) (MPC-Gr), a copolymer of MPC, Gr, and butyl methacrylate (BMA) (MPC-BMA-Gr), a copolymer of MPC, BMA, and hydroxyethyl methacrylate (HMA) (MPC-BMA-HMA), a copolymer of MPC and HMA (MPC-HMA), and a copolymer of MPC and BMA (MPC-BMA) were synthesized.

Specifically, the following seven kinds of polymers 1 to 7 were synthesized.

Polymer 1: MPC-BMA-Gr copolymer A (MPC/BMA/Gr=40/20/40=phosphorylcholine group-containing polymer/polymer having a hydrophobic group/polymer having a hydroxy group) weight-average molecular weight: 100 kDa Polymer 2: MPC-BMA-Gr copolymer B (MPC/BMA/Gr=40/40/20=phosphorylcholine group-containing polymer/polymer having a hydrophobic group/polymer having a hydroxy group) weight-average molecular weight: 100 kDa Polymer 3: MPC-BMA-HMA copolymer (MPC/BMA/HMA=20/20/60=phosphorylcholine group-containing polymer/polymer having a hydrophobic group/polymer having a hydroxy group) weight-average molecular weight: 1,000 kDa Polymer 4: MPC-Gr copolymer (MPC/Gr=50/50=phosphorylcholine group-containing polymer/polymer having a hydroxy group) weight-average molecular weight: 300 kDa Polymer 5: MPC-HMA copolymer (MPC/HMA=70/30=phosphorylcholine group-containing polymer/polymer having a hydroxy group) weight-average molecular weight: 500 kDa Polymer 6: MPC-BMA copolymer (MPC/BMA=80/20=phosphorylcholine group-containing polymer/polymer having a hydrophobic group) weight-average molecular weight: 600 kDa Polymer 7: MPC-BMA copolymer (MPC/BMA=30/70=phosphorylcholine group-containing polymer/polymer having a hydrophobic group) weight-average molecular weight: 100 kDa (In the parentheses, the molar ratio of each polymer in a feed composition and the polymer having each group are shown.)

The monomers for each polymer were weighed into a polymerization vessel. A mixed solvent of ethanol and water was used as a reaction solvent, and the total monomer concentration was adjusted to 1.0 mol/L. Then, to the weighed monomers, azobisisobutyronitrile (AIBN) was added as a polymerization initiator. The concentration of the polymerization initiator was set to 1 mol %.

Next, the air inside the polymerization vessel was sufficiently replaced with nitrogen, and then the polymerization vessel was kept at 60° C. for 24 hours to perform a polymerization reaction. Then, the resultant reaction mixture was cooled with ice, and then added dropwise to diethyl ether to precipitate a polymer. The precipitated polymer was separated by filtration, washed with diethyl ether, and then dried under reduced pressure. Thus, each polymer was obtained as white powder. Each obtained polymer was dissolved in pure water and stored as a 5 wt % aqueous solution.

Each obtained polymer was subjected to elemental analysis. As a result, it was confirmed that a copolymer having the feed composition had been obtained.

(Measurement Method for Non-Specific Protein Adsorption-Suppressing Ability)

The synthesized polymers 1 to 7, and partially saponified polyvinyl alcohol (PVA-205 manufactured by Kuraray Co., Ltd.) and bovine serum albumin (BSA) were each dissolved in Dulbecco's phosphate-buffered saline (manufactured by Sigma-Aldrich, hereinafter referred to as "D-PBS") at 1 wt % to produce solid phase-treating liquids containing the respective polymers, and a BSA solution and a D-PBS solution serving as controls.

Next, the solid phase-treating liquid containing each polymer, the BSA solution, or the D-PBS solution, which had been prepared at 1 wt %, was dispensed into a 96-well plate made of polycarbonate (300 µL/well), and incubated at 25° C. for 3 hours. Further, after the incubation for 3 hours, the solution was completely removed with an aspirator, and the plate was washed five times by repeatedly dispensing and removing D-PBS at 300 µL/well.

As an artificial serum solution, a D-PBS artificial serum solution containing human serum albumin at 50 mg/mL and human immunoglobulin G (human IgG) at 10 mg/mL was prepared.

10% artificial serum solutions each containing, at a final concentration of 1%, any one of the synthesized polymers 1 to 7 and partially saponified polyvinyl alcohol, the BSA solution, or D-PBS (containing any one of the specimen-treating liquids, or the polymer 4, the polymer 5, the BSA solution, or the D-PBS solution serving as a control) were prepared.

The 10% artificial serum solution containing each specimen-treating liquid, the 10% artificial serum solution containing the polymer 4 serving as a control, the 10% artificial serum solution containing the polymer 5 serving as a control, the 10% artificial serum solution containing the BSA solution serving as a control, or the 10% artificial serum solution containing the D-PBS solution serving as a control was dispensed into a 96-well plate made of polycarbonate (300 µL/well), and incubated at 25° C. for 1 hour. After 1 hour, the solution was completely removed with an aspirator, and the plate was washed five times by repeatedly dispensing and removing D-PBS (300 µL/well).

A peroxidase-labeled anti-human immunoglobulin G antibody (POD-anti-human IgG antibody, manufactured by Rockland) diluted 5,000-fold was dispensed (100 µL/well), and incubated at 25° C. for 1 hour. After 1 hour, the solution was completely removed with an aspirator, and the plate was washed five times by repeatedly dispensing and removing D-PBS at 300 µL/well. After the washing, TMB Microwell Peroxidase Substrate (manufactured by MOSS) was added at 100 µL/well, and a reaction was performed at 25° C. for 15 minutes. The color reaction was stopped by dispensing a 0.3 mol/L sulfuric acid solution (100 µL/well), and an absorbance at 450 nm was measured to detect an adsorbed protein.

A solid phase used, and combinations of solid phase-treating liquids and specimen-treating liquids were as described below.

Example 1-1

Untreated polycarbonate was used for the solid phase, and protein adsorption-suppressing abilities were measured for the combinations shown in Table 1.

Example 1-2

Untreated polystyrene was used for the solid phase, and protein adsorption-suppressing abilities were measured for the combinations shown in Table 2.

Example 1-3

Untreated polymethylmethacrylate was used for the solid phase, and protein adsorption-suppressing abilities were measured for the combinations shown in Table 3.

Example 1-4

Maxisorp (manufactured by Thermo Fischer Scientific Inc.) was used for the solid phase, and protein adsorption-suppressing abilities were measured for the combinations shown in Table 4.

Comparative Example 1-1

Untreated polycarbonate was used for the solid phase, and protein adsorption-suppressing abilities were measured for the combinations shown in Table 1.

Comparative Example 1-2

Untreated polystyrene was used for the solid phase, and protein adsorption-suppressing abilities were measured for the combinations shown in Table 2.

Comparative Example 1-3

Untreated polymethylmethacrylate was used for the solid phase, and protein adsorption-suppressing abilities were measured for the combinations shown in Table 3.

Comparative Example 1-4

Maxisorp (manufactured by Thermo Fischer Scientific Inc.) was used for the solid phase, and protein adsorption-suppressing abilities were measured for the combinations shown in Table 4.

The measurement results of the non-specific protein adsorption-suppressing abilities of Examples 1-1, 1-2, 1-3, and 1-4, and Comparative Examples 1-1, 1-2, 1-3, and 1-4 are shown in Table 1 to Table 4 below.

TABLE 1

|  | Solid phase-treating liquid or control | Specimen-treating liquid or control | Absorbance (450 nm) |
| --- | --- | --- | --- |
| Example 1-1-1 | Polymer 1 | Polymer 2 | 0.0040 |
| Example 1-1-2 | Polymer 3 | Polymer 2 | 0.0060 |
| Example 1-1-3 | Polymer 6 | Polymer 1 | 0.0080 |
| Example 1-1-4 | Polymer 7 | Polymer 1 | 0.0080 |
| Comparative Example 1-1-1 | BSA | BSA | 0.0510 |
| Comparative Example 1-1-2 | Polymer 2 | BSA | 0.0650 |
| Comparative Example 1-1-3 | Polymer 2 | Polymer 4 | 0.0950 |
| Comparative Example 1-1-4 | D-PBS | D-PBS | 0.7050 |

TABLE 2

|  | Solid phase-treating liquid or control | Specimen-treating liquid or control | Absorbance (450 nm) |
| --- | --- | --- | --- |
| Example 1-2-1 | Polymer 6 | Polymer 2 | 0.0140 |
| Example 1-2-2 | Polymer 1 | Polymer 2 | 0.0140 |
| Example 1-2-3 | Polymer 6 | Polymer 3 | 0.0180 |
| Example 1-2-4 | Polymer 6 | Polymer 1 | 0.0180 |
| Comparative Example 1-2-1 | BSA | BSA | 0.0200 |
| Comparative Example 1-2-2 | PVA | Polymer 1 | 0.0290 |
| Comparative Example 1-2-3 | Polymer 7 | Polymer 4 | 0.0300 |
| Comparative Example 1-2-4 | D-PBS | D-PBS | 0.1170 |

TABLE 3

| | Solid phase-treating liquid or control | Specimen-treating liquid or control | Absorbance (450 nm) |
|---|---|---|---|
| Example 1-3-1 | Polymer 1 | Polymer 1 | 0.0050 |
| Example 1-3-2 | Polymer 6 | Polymer 2 | 0.0060 |
| Example 1-3-3 | Polymer 7 | Polymer 1 | 0.0060 |
| Example 1-3-4 | Polymer 4 | Polymer 1 | 0.0100 |
| Comparative Example 1-3-1 | BSA | BSA | 0.0830 |
| Comparative Example 1-3-2 | Polymer 2 | Polymer 5 | 0.0910 |
| Comparative Example 1-3-3 | Polymer 6 | Polymer 4 | 0.1620 |
| Comparative Example 1-3-4 | D-PBS | D-PBS | 0.1210 |

TABLE 4

| | Solid phase-treating liquid or control | Specimen-treating liquid or control | Absorbance (450 nm) |
|---|---|---|---|
| Example 1-4-1 | Polymer 5 | Polymer 3 | 0.0400 |
| Example 1-4-2 | Polymer 4 | Polymer 1 | 0.0410 |
| Example 1-4-3 | Polymer 3 | Polymer 2 | 0.0420 |
| Example 1-4-4 | Polymer 6 | Polymer 3 | 0.0890 |
| Comparative Example 1-4-1 | BSA | BSA | 0.4120 |
| Comparative Example 1-4-2 | Polymer 1 | Polymer 5 | 1.2380 |
| Comparative Example 1-4-3 | Polymer 7 | Polymer 5 | 1.9400 |
| Comparative Example 1-4-4 | D-PBS | D-PBS | 2.1110 |

From the measurement results of the non-specific protein adsorption-suppressing abilities of Table 1 to Table 4 above, it was confirmed that in the method of suppressing non-specific protein adsorption of the present invention using the solid phase-treating liquid containing a phosphorylcholine group-containing polymer as a main component, and the specimen-treating liquid containing, as a main component, a polymer having a phosphorylcholine group, a hydroxy group, and a hydrophobic group, the polymers contained in the solid phase-treating liquid and specimen-treating liquid used, which were chemically synthesized products, had high non-specific protein adsorption-suppressing abilities.

The non-specific protein adsorption-suppressing abilities of Comparative Examples 1-1-3, 1-2-3, 1-3-2, 1-3-3, 1-4-2, and 1-4-3 are low because the specimen-treating liquid does not contain a polymer having a hydrophobic group.

INDUSTRIAL APPLICABILITY

The present invention can provide the novel method of suppressing non-specific protein adsorption.

The invention claimed is:

1. A method of suppressing non-specific protein adsorption, the method comprising the steps of:
   (A) (i) treating a solid phase material with a solid phase-treating liquid containing a phosphorylcholine group-containing polymer as a main component; and
   (ii) treating a specimen with a specimen-treating liquid containing, as a main component, a polymer having a phosphorylcholine group, a hydroxy group, and a hydrophobic group, followed by addition of the treated specimen to the solid phase treated in the step (i), or
   (B) (iii) treating a specimen with a specimen-treating liquid containing, as a main component, a polymer having a phosphorylcholine group, a hydroxy group, and a hydrophobic group; and
   (iv) treating a solid phase material with a solid phase-treating liquid containing a phosphorylcholine group-containing polymer as a main component, followed by addition of the specimen treated in the step (iii) to the treated solid phase.

2. A method of suppressing non-specific protein adsorption according to claim 1, wherein a combination of the phosphorylcholine group-containing polymer, and the polymer having a phosphorylcholine group, a hydroxy group, and a hydrophobic group comprises:
   (1) a combination of
   a phosphorylcholine group-containing polymer which contains, as constituent units, 2-methacryloyloxyethylphosphorylcholine, butyl methacrylate, and glycerol methacrylate, and a polymer having a phosphorylcholine group, a hydroxy group, and a hydrophobic group, which contains, as constituent units, 2-methacryloyloxyethylphosphorylcholine, butyl methacrylate, and glycerol methacrylate.

3. A method of suppressing non-specific protein adsorption according to claim 1, wherein a combination of the phosphorylcholine group-containing polymer, and the polymer having a phosphorylcholine group, a hydroxy group, and a hydrophobic group comprises:
   (2) a combination of
   a phosphorylcholine group-containing polymer which contains, as constituent units, 2-methacryloyloxyethylphosphorylcholine, butyl methacrylate, and hydroxyethyl methacrylate, and
   a polymer having a phosphorylcholine group, a hydroxy group, and a hydrophobic group, which contains, as constituent units, 2-methacryloyloxyethylphosphorylcholine, butyl methacrylate, and glycerol methacrylate.

4. A method of suppressing non-specific protein adsorption according to claim 1, wherein a combination of the phosphorylcholine group-containing polymer, and the polymer having a phosphorylcholine group, a hydroxy group, and a hydrophobic group comprises:
   (3) a combination of
   a phosphorylcholine group-containing polymer which contains, as constituent units, 2-methacryloyloxyethylphosphorylcholine and butyl methacrylate, and
   a polymer having a phosphorylcholine group, a hydroxy group, and a hydrophobic group, which contains, as constituent units, 2-methacryloyloxyethylphosphorylcholine, butyl methacrylate, and glycerol methacrylate.

5. A method of suppressing non-specific protein adsorption according to claim 1, wherein a combination of the phosphorylcholine group-containing polymer, and the polymer having a phosphorylcholine group, a hydroxy group, and a hydrophobic group comprises:
   (4) a combination of
   a phosphorylcholine group-containing polymer which contains, as constituent units, 2-methacryloyloxyethylphosphorylcholine and butyl methacrylate, and
   a polymer having a phosphorylcholine group, a hydroxy group, and a hydrophobic group, which contains, as constituent units, 2-methacryloyloxyethylphosphorylcholine, butyl methacrylate, and hydroxyethyl methacrylate.

6. A method of suppressing non-specific protein adsorption according to claim 1, wherein a combination of the phosphorylcholine group-containing polymer, and the polymer having a phosphorylcholine group, a hydroxy group, and a hydrophobic group comprises:

(5) a combination of a phosphorylcholine group-containing polymer which contains, as constituent units, 2-methacryloyloxyethylphosphorylcholine and glycerol methacrylate, and a polymer having a phosphorylcholine group, a hydroxy group, and a hydrophobic group, which contains, as constituent units, 2-methacryloyloxyethylphosphorylcholine, butyl methacrylate, and glycerol methacrylate.

7. A method of suppressing non-specific protein adsorption according to claim 1, wherein a combination of the phosphorylcholine group-containing polymer, and the polymer having a phosphorylcholine group, a hydroxy group, and a hydrophobic group comprises:

(6) a combination of a phosphorylcholine group-containing polymer which contains, as constituent units, 2-methacryloyloxyethylphosphorylcholine and hydroxyethyl methacrylate, and a polymer having a phosphorylcholine group, a hydroxy group, and a hydrophobic group, which contains, as constituent units, 2-methacryloyloxyethylphosphorylcholine, butyl methacrylate, and hydroxyethyl methacrylate.

* * * * *